US005705506A

United States Patent [19]

Merlet et al.

[11] Patent Number: 5,705,506
[45] Date of Patent: Jan. 6, 1998

[54] PHARMACEUTICAL COMPOSITIONS OF ALKYLSULPHONAMIDES 5HT1 AGONISTS FOR RECTAL ADMINISTRATION

[75] Inventors: Nadine Merlet; Isabelle Richard; Isabelle Thielemans, all of Evreux, France

[73] Assignee: Laboratoires Glaxo SA, Paris, France

[21] Appl. No.: 331,485

[22] PCT Filed: May 3, 1993

[86] PCT No.: PCT/EP93/01077

§ 371 Date: Dec. 29, 1994

§ 102(e) Date: Dec. 29, 1994

[87] PCT Pub. No.: WO93/21916

PCT Pub. Date: Nov. 11, 1993

[30] Foreign Application Priority Data

May 7, 1992 [GB] United Kingdom ............ 9209882

[51] Int. Cl.⁶ ............................................ A01N 43/42
[52] U.S. Cl. ............ 514/310; 514/323; 514/374; 514/378; 514/385; 514/406; 514/414; 514/415; 548/504; 548/505
[58] Field of Search ............. 514/310, 415, 514/323, 374, 378, 385, 406, 414; 548/504, 505

[56] References Cited

U.S. PATENT DOCUMENTS

| 4,785,016 | 11/1988 | Evans et al. ............ 514/415 |
| 4,994,483 | 2/1991 | Oxford et al. ........... 514/415 |
| 5,037,845 | 8/1991 | Oxford .................. 514/415 |

FOREIGN PATENT DOCUMENTS

| A-0 303 507 | 2/1989 | European Pat. Off. |
| A-2 162 522 | 2/1986 | United Kingdom . |
| 91/18897 | 12/1991 | WIPO . |

OTHER PUBLICATIONS

Arnold, *Neurol. Neurochir. Pol.*, 26, No. S.2, 1992, 49–56.
Klapper, *Headache Quart.*, 2, No. 2, 1991, 83–90.

Primary Examiner—Nathan M. Nutter
Assistant Examiner—Duc Truong
Attorney, Agent, or Firm—Bacon & Thomas

[57] ABSTRACT

The present invention relates to a pharmaceutical composition for rectal administration in solid dosage form which comprises a compound acting as a 5HT-1 like receptor agonist in the form of its free base or a physiologically acceptable hard fat base carrier having a hydroxyl value of more than 15 in the method for the treatment of a mammal suffering from a susceptible to conditions associated with cephalic pain.

23 Claims, No Drawings

PHARMACEUTICAL COMPOSITIONS OF ALKYLSULPHONAMIDES 5HT1 AGONISTS FOR RECTAL ADMINISTRATION

This application is a 371 of PCT/EP 93/01077 filed May 3, 1993.

The present invention relates to a pharmaceutical composition containing as active ingredient a compound having selective agonist activity at $5HT_1$-like receptors, in particular a composition for rectal administration.

$5$-$HT_1$-like receptors are located, for example, in the dog saphenous vein and the $5$-$HT_1$-like receptor agonists with which the present invention is concerned contract the dog saphenous vein. Such compounds may therefore be identified by their contractile effect on the dog isolated saphenous vein strip as described, for example, by Apperley et al., Br. J. Pharmacol, 68, 215–224 (1980). Compounds which are selective $5$-$HT_1$-like receptor agonists have also been found to selectively constrict the carotid arterial bed of the anaesthetised dog.

A variety of compounds which selectively constrict the dog isolated saphenous vein strip and which constrict the carotid arterial bed of the anaesthetised dog have been described in the art. These include indole derivatives such as those disclosed inter alia in published British Patent Specifications Nos. 2082175, 2081717, 2083463, 2124210, 2150932, 2162522, 2168347, 2168973, 2185020, 2186874, 2191488, 2208646, published European Patent Specifications Nos. 147107, 237678, 242939, 244085, 225726, 254433, 303506, 313397, 354777, 382570, 464558, 506363, 506369, 450238, 451022, 451008, 478954, 438230, 494774, 497512, 501568 and published International patent application Nos. WO92/11013, WO92/11014, WO92/06973, WO93/00086, WO92/13856, WO93/00094, WO91/18897 and WO93/00333. The compounds disclosed in the specifications (hereinafter described as compounds A) are useful in the treatment of migraine and cluster headache.

Oral administration constitutes the generally preferred route for administration of pharmaceuticals since this route is particularly convenient and acceptable to patients. Unfortunately oral compositions may be associated with certain disadvantages, particularly in the treatment of conditions such as migraine which may be accompanied by nausea and/or vomiting. Furthermore, migraine is associated with delayed gastric emptying which may lead to both a delay and an impairment of drug absorption following oral administration. It is highly desirable, particularly in the treatment of acute conditions such as migraine, that pharmaceutical compositions have a rapid and consistent onset of action combined with sustained activity and good bioavailability. Rapid absorption can be achieved by parenteral injection but this is unacceptable to some patients, particularly if the drug is to be administered without direct medical supervision, i.e. self-administered.

The present invention provides a pharmaceutical composition for rectal administration which comprises a compound which acts as a $5HT_1$-like receptor agonist in the form of its free base or a physiologically acceptable solvate thereof as active ingredient, together with one or more pharmaceutically acceptable carriers or excipients.

In a preferred embodiment of the invention we provide a pharmaceutical composition for rectal administration which comprises one or more of compounds A in the form of its free base or a pharmaceutically acceptable solvate thereof as active ingredient.

Compositions according to the invention are preferably in a form adapted for use in medicine, in particular human medicine.

Particularly preferred compounds for use in the compositions of the present invention are 3-[2-(dimethylamino)ethyl]-N-methyl-1H-indole-5-methanesulphonamide and N-methyl-3-(1-methyl-4-piperidinyl)-1H-indole-5-ethanesulphonamide, especially 3-[2-(dimethylamino)ethyl]-N-methyl-1H-indole-5-methanesulphonamide.

3-[2-(Dimethylamino)ethyl]-N-methyl-1H-indole-5-methanesulphonamide, which may be represented by the formula (I)

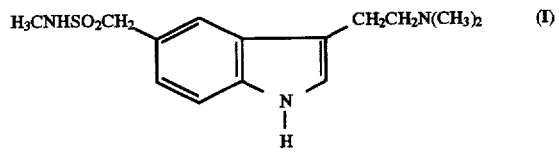

and its physiologically acceptable salts and solvates are disclosed in GB 2162522. The compound of formula (I) is described as useful in treating and/or preventing pain resulting from dilatation of the cranial vasculature, in particular migraine.

Numerous clinical studies have demonstrated the effectiveness of the compound of formula (I) in migraineurs. Hitherto, the drug has always been administered in the form of a salt, for example its succinate (1:1) salt, either by oral or intranasal administration or by parenteral injection.

Alternative routes for administration of the compound of formula (I) are proposed in GB 2162522 including rectal administration. GB 2162522 specifically discloses a number of pharmaceutical formulations containing 3-[2-(dimethylamino)ethyl]-N-methyl-1H-indole-5-methanesulphonamide succinate (1:1) as active ingredient, including a suppository formulation for rectal administration.

The present invention provides a particularly advantageous pharmaceutical formulation, not specifically disclosed in GB 2162522, which is suitable for rectal administration of the compound of formula (I).

There is thus provided in a particularly preferred aspect of the invention a pharmaceutical composition for rectal administration which comprises 3-[2-(dimethylamino)ethyl]-N-methyl-1H-indole-3-methanesulphonamide or a pharmaceutically acceptable solvate thereof as active ingredient, together with one or more pharmaceutically acceptable carriers or excipients.

Unlike the prior art compositions, the compositions according to the invention contain the active ingredient in the form of its free base or a pharmaceutically acceptable solvate thereof. The applicants have found that the use of the free base rather than the succinate salt of the compound of formula (I) is surprisingly advantageous when the active ingredient is administered rectally.

It is highly desirable in the treatment of acute conditions such as migraine that pharmaceutical compositions have good bioavailability and a rapid onset of action. Suppository formulations according to the present invention have been determined to have excellent pharmacokinetic parameters. When compared to suppository formulations containing 3-[2-(dimethylamino)ethyl]-N-methyl-1H-indole-5-methanesulphonamide salt (succinate 1:1 salt), formulations according to the present invention surprisingly result in a more rapid and complete absorption of the active ingredient.

The compositions according to the invention may be in the form of retention enemas or solid dosage forms such as suppositories or soft gelatin capsules. Preferably the compositions are formulated as solid unit dosage forms suitably shaped, for example conical, cylindrical or torpedo-shaped, for rectal administration. The solid dosage forms may either melt at body temperature or dissolve or disperse in the mucous secretions of the cavity.

Conventional carriers which may be employed in the compositions according to the invention include theobroma oil, hard fats, glycerol-gelatin bases, macrogols (polyethylene glycols) and mixtures thereof. Preferred compositions comprise hard fat bases such as esterified, hydrogenated or fractionated vegetable oils and synthetic triglyceride mixtures produced under the name of adeps solidus.

Preferred bases are hard fats containing a mixture of mono-, di- and triglycerides of saturated $C_{9-18}$ fatty acids. Preferably the base has a high Hydroxyl Value (USP Chemical Test), for example a Hydroxyl Value of more than 10, preferably more than 15, especially in the range of 20 to 100, for example 40 to 50.

Solid dosage forms such as suppositories may be prepared in conventional manner for example by intimate admixture of the active ingredient with the carrier, preferably the molten carrier. Preferably the active ingredient is micronised prior to incorporation into the molten base, for example such that at least 90% of the active ingredient (particle number measured using a Malvern particle size laser) is in the form of particles having a particle size of 10 microns or less, preferably 5 microns diameter or less, for example about 2 microns. The molten composition may then be poured into suitable moulds, for example PVC, polyethylene or aluminium moulds. Optionally the suppositories may be coated, prior to packing, for example with cetyl alcohol, macrogol or polyvinyl alcohol and polysorbates to increase disintegration time or lubrication or to reduce adhesion on storage.

Preferably the total weight of the solid dosage form is about 1 or 2 grams and the active ingredient may comprise 0.1 to 20% by weight of the composition, preferably 0.5 to 10% by weight of the composition.

The amount of active ingredient, for example 3-[2-(dimethylamino)ethyl]-N-methyl-1H-indole-5-methanesulphonamide, employed in the compositions of the invention will preferably be in the range of about 1 mg to about 200 mg, most preferably about 5 mg to about 100 mg, especially 5 to 30 mg.

A further aspect of the invention provides, a method for the treatment of a mammal, including man, suffering from or susceptible to conditions associated with cephalic pain such as duster headache, chronic paroxysmal hemicrania, headache associated with vascular disorders, headache associated with substances or their withdrawal (for example drug withdrawal), tension headache and in particular migraine which comprises rectal administration of a pharmaceutical composition which comprises a compound which acts as a $5HT_1$-like receptor agonist, for example 3-[2-(dimethylamino)ethyl]-N-methyl-1H-indole-5-methanesulphonamide or a pharmaceutically acceptable solvate thereof as active ingredient, together with one or more pharmaceutically acceptable carriers or excipients. It will be appreciated that reference to treatment is intended to include prophylaxis as well as the alleviation of established symptoms.

It will be appreciated that the amount of compounds which act as $5HT_1$-like receptor agonists employed in the compositions of the invention will depend on the particular compounds used. Furthermore, the precise therapeutic dose of the active ingredient will depend on the age and condition of the patient and the nature of the condition to be treated and will be at the ultimate discretion of the attendant physician.

However, in general, effective doses for the treatment of conditions associated with cephalic pain, for example acute treatment of migraine, will lie in the range of 1 to 500 mg, preferably 2 to 200 mg, most preferably 5 to 100 mg, for example 10 mg or 25 mg of the active ingredient per unit dose which could be administered in single or divided doses, for example, 1 to 4 times per day.

The invention is further illustrated by the following non-limiting examples.

EXAMPLE 1

| Suppository for Rectal Administration | Unit Formula (per suppository) |
|---|---|
| 3-[2-(Dimethylamino)ethyl]-N-methyl-1H-indole-5-methanesulphonamide (micronised free base) | 25 mg |
| Adeps Solidus Ph. Eur. (sold under the trade name Witepsol W32) Hydroxyl Value 30–40 | to 2 g |

A suspension of the active ingredient in molten base was prepared and filled in conventional manner into 2 g size suppository moulds.

EXAMPLES 2 TO 5

Suppositories containing 6, 12.5, 50 or 100 mg 3-[2-(dimethylamino)ethyl]-N-methyl-1H-indole-5-methanesulphonamide (micronised free base) were prepared as described for the suppositories of Example 1.

EXAMPLES 6–10

Suppositories containing 1, 2.5, 5, 10 or 25 mg N-methyl-3-(1-methyl-4-piperidinyl)-1H-indole-5-ethanesulphonamide (micronised free base) were prepared as described for the suppositories of Example 1.

We claim:

1. A pharmaceutical composition for rectal administration in solid dosage form which comprises an effective amount of a compound which acts as a $5HT_1$-like receptor agonist in the form of its free base or a physiologically acceptable solvate thereof as active ingredient and a pharmaceutically acceptable hard fat base carrier having a Hydroxyl Value of more than 15.

2. A pharmaceutical composition as claimed in claim 1 wherein the active ingredient is selected from the group consisting of 3-[2-(dimethylamino)ethyl]-N-methyl-1H-indole-5-methanesulphonamide N-methyl-3-(1-methyl-4-piperidinyl)-1H-indole-5-ethanesulphonamide and pharmaceutically acceptable solvates thereof.

3. A pharmaceutical composition as claimed in claim 1 wherein the active ingredient 3-[2-(dimethylamino)ethyl]-N-methyl-1H-indole-5-methanesulphonamide or a pharmaceutically acceptable solvate thereof.

4. A pharmaceutical composition as claimed in claim 1 wherein the active ingredient is N-methyl-3-(1-methyl-4-piperidinyl)-1H-indole-5-ethanesulphonamide or a pharmaceutically acceptable solvate thereof.

5. A pharmaceutical composition as claimed in claim 1 in the form of a suppository.

6. A pharmaceutical composition as claimed in claim 1 wherein the hard fat base has a Hydroxyl Value in the range of 20 to 100.

7. A pharmaceutical composition as claimed in claim 1 which comprises 0.1 to 20% by weight of active ingredient.

8. A pharmaceutical composition as claimed in claim 1 which comprises about 1 to about 200 mg of active ingredient.

9. A pharmaceutical composition as claimed in claim 8 which comprises 5 to 30 mg of active ingredient.

10. A pharmaceutical composition as claimed in claim 1 wherein the active ingredient is micronised.

11. A method for the treatment of a mammal, including man, suffering from or susceptible to conditions associated with cephalic pain such as cluster headache, chronic paroxysmal hemicrania, headache associated with vascular disorders, headache associated with substances or their withdrawal (for example drug withdrawal), tension headache and in particular migraine which comprises rectal administration of a pharmaceutical composition comprising a compound which acts as a $5HT_1$-like receptor agonist in the form of its free base or a pharmaceutically acceptable solvate thereof.

12. A method as claimed in claim 11 wherein the $5HT_1$-like receptor agonist is 3-[2-(dimethylamino)ethyl]-N-methyl-1H-indole-5-methanesulphonamide or a pharmaceutically acceptable solvate thereof.

13. A pharmaceutical composition as claimed in claim 3 in the form of a suppository.

14. A pharmaceutical composition as claimed in claim 3 wherein the hard fat base has a Hydroxyl Value in the range of 20 to 100.

15. A pharmaceutical composition as claimed in claim 5 wherein the hard fat base has a Hydroxyl Value in the range of 20 to 100.

16. A pharmaceutical composition as claimed in claim 3 which comprises 0.1 to 20% by weight of active ingredient.

17. A pharmaceutical composition as claimed in claim 5 which comprises 0.1 to 20% by weight of active ingredient.

18. A pharmaceutical composition as claimed in claim 6 which comprises 0.1 to 20% by weight of active ingredient.

19. A pharmaceutical composition as claimed in claim 3 which comprises about 1 to 200 mg of active ingredient.

20. A pharmaceutical composition as claimed in claim 5 which comprises about 1 to 200 mg of active ingredient.

21. A pharmaceutical composition as claimed in claim 6 which comprises about 1 to 200 mg of active ingredient.

22. A pharmaceutical composition as claimed in claim 7 which comprises about 1 to 200 mg of active ingredient.

23. A pharmaceutical composition as claimed in claim 3 which comprises 5 to 30 mg of active ingredient.

* * * * *